United States Patent [19]

Szapiro et al.

[11] Patent Number: 5,785,683
[45] Date of Patent: Jul. 28, 1998

[54] DISPOSABLE SYRINGE WITH TWO VARIABLE VOLUME CHAMBERS

[76] Inventors: Jaime Luis Szapiro; Leonardo Szames; Saul Moreno, all of Tabaré 1641, Buenos Aires, Argentina

[21] Appl. No.: 611,407

[22] Filed: Mar. 6, 1996

[30] Foreign Application Priority Data

Jul. 17, 1995 [AR] Argentina ............ 332787

[51] Int. Cl.$^6$ .................................. A61M 37/00
[52] U.S. Cl. ........................... 604/89; 604/228
[58] Field of Search ............ 604/82–89, 218, 604/228, 222, 191

[56] References Cited

U.S. PATENT DOCUMENTS

| | | | |
|---|---|---|---|
| 3,464,412 | 9/1969 | Schwartz | 604/89 |
| 3,511,239 | 5/1970 | Tuschhoff | 604/89 |
| 3,680,558 | 8/1972 | Kapleowitz | 604/89 |
| 4,610,669 | 9/1986 | Meyer et al. | 604/218 |
| 4,613,326 | 9/1986 | Szwarc | 604/89 |
| 5,226,881 | 7/1993 | Pickhard | 604/110 |
| 5,246,423 | 9/1993 | Farkas | 604/110 |

Primary Examiner—Michael Buiz
Assistant Examiner—A. T. Nguyen
Attorney, Agent, or Firm—Bachman & LaPointe, P.C.

[57] ABSTRACT

The invention relates to a pre-filled disposable syringe to be used in the administration of powdered drug diluted at the time of injection. The novelty resides in that the plunger head, along with an elastomer head, constitute a particular valve acting as a function of plunger displacements.

5 Claims, 3 Drawing Sheets

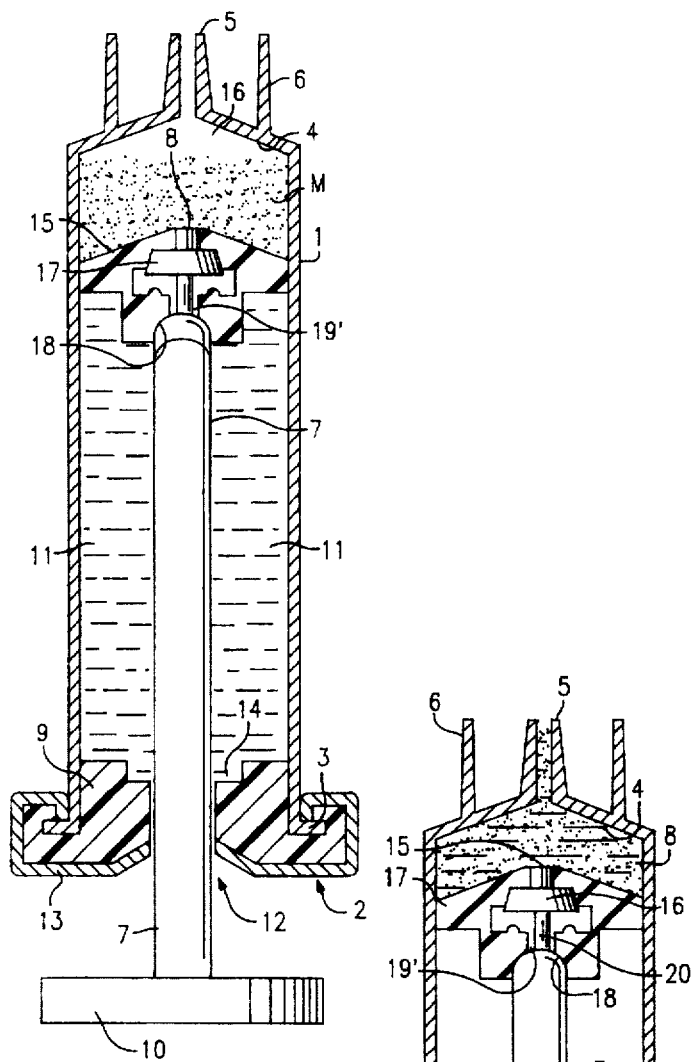
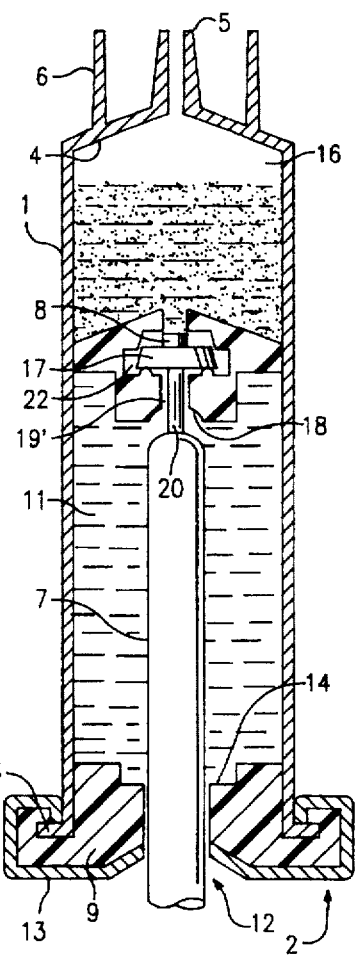
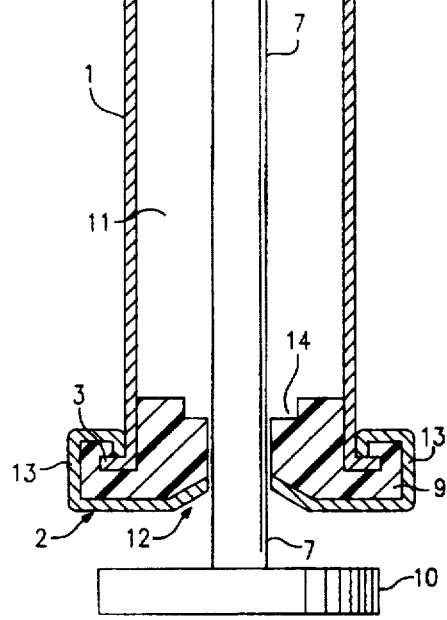
FIG. 5
FIG. 6
FIG. 7

DISPOSABLE SYRINGE WITH TWO VARIABLE VOLUME CHAMBERS

I. FIELD OF THE INVENTION—PRIOR ART

The instant invention relates to a disposable syringe with two variable volume chambers for administering liquid products or diluted powdered drugs. These syringes are of the type commercialized with the product already contained therein. They are also suitable for including, separately, powdered drug and a diluent, which are mixed at the time of injection. Therefore, they are included in the group usually called pre-filled syringes, since they are already provided with the medicine, thus assuring no contact of the user with the drug.

More particularly, the instant invention relates to a syringe of the above mentioned type comprised by a main cylindrical, hollow body, containing the medicine to be administered, and through which a coaxial plunger is located. In all cases the lower base of said main cylindrical body has an opening through which the rear end of said coaxial plunger projects, and has an annular flange in order that the user may push or pull manually the plunger. Further, at the opposite base of said main body, there is a hollow, coaxial and generally frusto-conical nozzle, constituting the plugging means for coupling and fixing the injection needle, which is housed inside a protecting sheath removably coupled to said upper base of the main body.

Several syringes like that defined above are already known. Most of them are syringes having a single tight chamber wherein the pharmaceutical product is housed; in this case, the plunger active head is located at the lower open base of the main body, displacing towards the opposite base, propelling the contents to the outlet nozzle wherein the injection needle is connected. The disadvantage of these syringes is that they are not suitable for containing powdered drugs since they have no resource for separating the drug from the diluent before injection, nor the means required for producing the mixture during injection.

Some kinds of pre-filled double chamber disposable syringes are also known. These are used for the cases in which the powdered drug is housed into one chamber and the diluent into the other chamber; simultaneous dilution and administration of the medicine being attained by the plunger displacement. In these cases, within said main body, there are two adjacent tight chambers, separated by valves which, through said plunger displacement, allow communication between chambers, thus mixing and diluting the drug.

Among double chamber syringes, that disclosed in Argentine patent No. 247,101, also filed in the U.S., is particularly incorporated as a reference.

Although results with the mentioned types of syringes are satisfactory, their construction is delicate, requires high precision and their cost is relatively high for disposable syringes.

A new pre-filled disposable syringe has been developed by the owner of the cited patent. This syringe may contain the powdered product and the diluent, duly separated, at the same time being a single chamber syringe. That is, the assembly may act as any conventional liquid product syringe or may be pre-filled with powdered drug and diluent, without modification thereof. In this case, the lower base of the main body is tightly closed by an elastomer plug including a conduit through which the plunger rod passes; the active head of said plunger being also an elastomer plug solidary to said rod, its peripheral edge bearing on the inner cylindrical surface of the main body and including to this end a flexible annular flange allowing liquid passage upwardly when the plunger descends; while during the upward stroke of the plunger, said peripheral annular flange causes the tight closure and displaces the product towards the nozzle connected to the injection needle.

The embodiment mentioned above constitutes an improvement over syringes with intermediate valve means due to economical reasons.

Nevertheless, the use of the flexible annular flange at the peripheral edge of the plunger head rather impairs tightness when liquid displaces towards the injection needle; also, liquid passage is not always assured when the plunger displaces in the reverse direction propelling liquid from the lower chamber to the upper chamber.

II. NOVELTY OF THE INVENTION

The syringe of the instant invention may act as pre-filled disposable syringe for powdered drugs and diluent, using a plunger having an elastomer active head acting as an intermediate partition.

In this case, the interior of the main body is also divided into two variable volume chambers; an upper chamber wherein the powdered drug is contained and a lower chamber housing the diluent.

When the plunger displaces in a direction opposite to that used for injection, the elastomer active head allows liquid passage towards the upper chamber, containing the powdered drug, thus attaining mixture and dilution thereof.

When such plunger displaces towards the nozzle connecting to the needle, i.e., during injection, the diluted product is easily administered to the patient.

The novel feature of the instant invention resides in that the active plunger head acts in combination with an elastomer head enclosing it, constituting in turn the tight closure separating adjacent variable volume chambers. The tight closure is produced by the peripheral edge of the elastomer head on the inner cylindrical surface of the main body. Passage of diluent to the upper part housing the powdered drug is produced through the central region of said elastomer head.

The central region of said elastomer head has a particular shape, cooperating with the plunger active head, producing a valve opening when the plunger descends towards the lower base of the main body; while a valve closure is attained when the plunger ascends towards the outlet nozzle to the injection needle.

III. BRIEF DESCRIPTION OF THE DRAWINGS

A preferred, non-limiting, embodiment of the invention will be hereinbelow described in connection with the accompanying drawings, in which:

The first sheet of drawings shows the invention when used for administering pre-filled liquid products with a disposable syringe.

Figure 1:
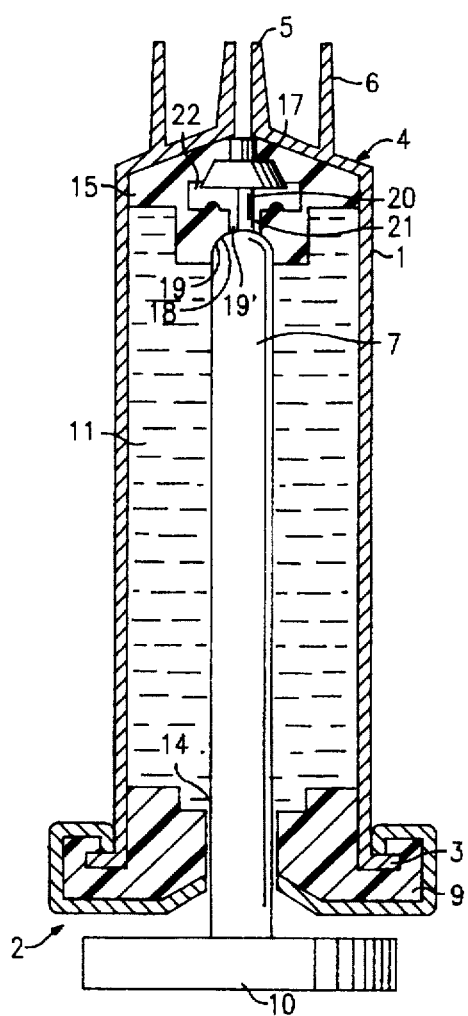
FIG. 1 is a longitudinal cross section of a disposable syringe showing the plunger of the invention.

The second sheet of drawings shows the invention when used for administering powdered drug diluted at the time of injection.

FIG. 5 is a longitudinal section showing the same syringe, with the products separated into adjacent chambers.

FIG. 6 is a longitudinal section showing mixing of the pre-filled products.

FIG. 7 is a longitudinal section showing schematically the operation of the assembly upon injection.

In all figures, the same reference numerals designate the same or equivalent elements.

IV. DETAILED DESCRIPTION OF THE INVENTION

As shown by the drawings, the disposable syringe of the instant invention is comprised by a main body 1, which is a straight axis circular cylinder; the lower base 2 is open and includes the conventional cantilever annular flange 3 employed by the user for operating the plunger. The substantially conical upper base 4 has the coaxial injection nozzle 5 which, along with the annular flange 6, defines the coupling for the plugging cone of the injection needle. Plunger 7 displaces through the interior, coaxial to said nozzle 5, which has the conventional rod projecting outwardly passing through plug 9 and ending at the broadening 10 required for manual operation thereof.

As shown by the drawings, plug 9 closing the lower opening 2, acts as a closure stop for the variable volume chamber 11. It is an elastomer plug having a central conduit 12 through which plunger 7 displaces with enough fitness for preventing liquid leakage from chamber 11. Such plug bears against the cylindrical wall of the main body and extends towards the sides for locking at said flange 3 of body 1. Such closure may be further obtained using special adhesives or pressure metal covers such as those shown by reference 13 in FIGS. 5, 6 and 7.

As shown by the drawings, the plug 9 has an annular cavity 14 located at the inner face surrounding said conduit 12; this produces an overlapping coupling when head 15 enclosing the plunger head is at its maximum lower point.

The novelty of the invention resides in the valve means defined by the active head 17 of the plunger and the elastomer head 15 enclosing it. In fact, said plunger 7 defines, adjacent its upper end, a cap-shaped seating edge 18 facing a lower cavity 19 of the elastomer head. Then, the plunger defines a short portion 20, narrower and longer than conduit 19 of said elastomer head. Finally, the end of the plunger constitutes its active head 17 housed into a valve inner cavity 22, defined at said elastomer head 15.

The apex 8 of elastomer head 15 is open, while the lower base of cavity 22 has teeth 21 constituting the bearing means for the plunger active head.

As shown in the figures, the frusto-conical shape of the active head 17 along with the shape of the apex portion 8, determine a particular valve opening and closure means allowing passage of the contents through the variable volume chambers 11 and 16.

In fact, FIG. 1 shows the syringe containing the liquid product to be administered, as marketed, i.e., with the head 15 acting as upper closure plug.

Figure 2:
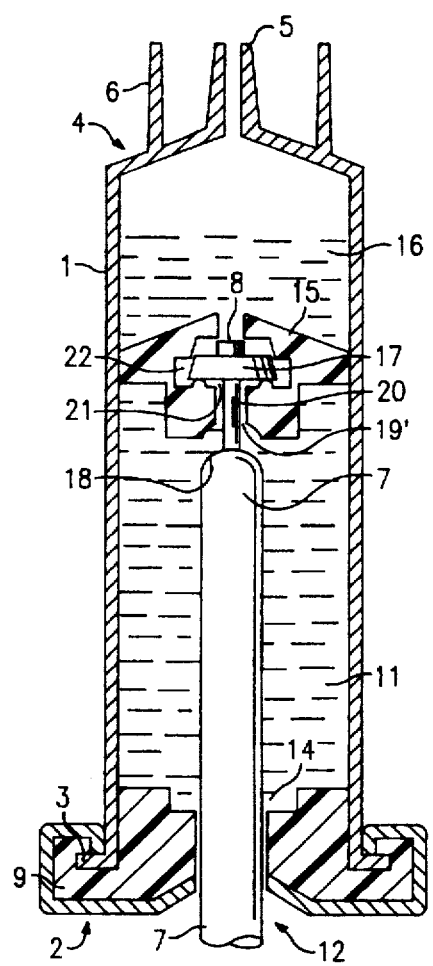
FIG. 2 is a longitudinal section with the plunger at the intermediate position.

FIG. 2 shows the way in which the user should displace the plunger to obtain passage of the contents from the lower chamber 11 to the upper chamber 16. The position adopted by the active head 17 allows passage of liquid through the inner cavity 22, and projection through the opening of apex 8.

Figure 3:
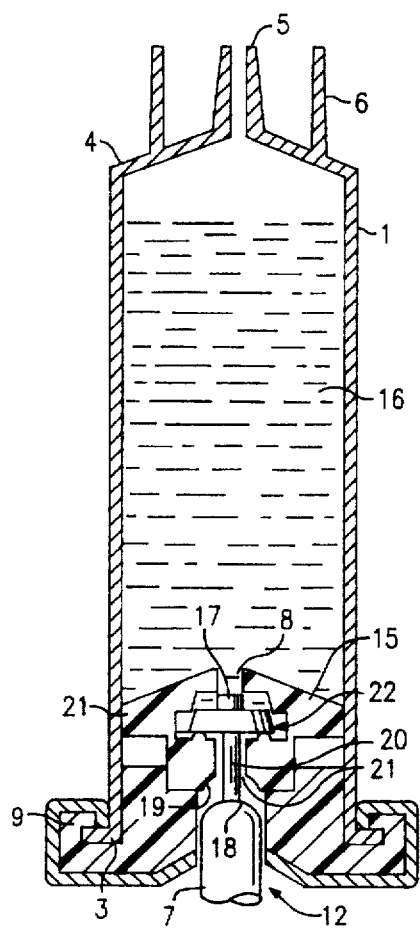
FIG. 3 is a longitudinal section, with the same plunger at a lower position and the injection chamber defined at its maximum capacity.

FIG. 3 shows the maximum outward expansion of plunger 7; herein, the elastomer head bears on the lower plug 9, the syringe being in condition of initiating the usual injection action.

Figure 4:
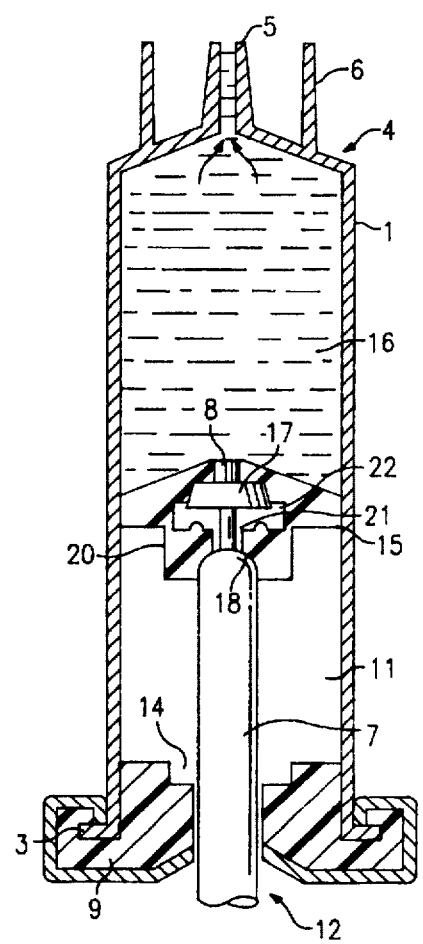
FIG. 4 is another longitudinal section, showing the action and arrangement of the valve means when injection is initiated.

FIG. 4 shows that, during the ascending stroke of plunger 7, the cap-shaped end thereof 18 produces valve closure on the lower seating cavity 19. Simultaneously, the frusto-conical surface of the active head 17 seats on the inner wall of the elastomer head 15 at the region adjacent its apex 8. In this way, liquid leakages are prevented during injection.

It is to be noted that other alternatives for the cooperating valve closure carried out by the elastomer head 15 and the active head 17 are also possible within the scope of the invention.

FIGS. 5, 6 and 7 show operation of the assembly (without any modification) when acting as pre-filled syringe containing powdered drug and diluent.

Solid material, at the upper region, designated with reference M, is separated from the diluent contained into chamber 11. Prior to injection, the user should shift the plunger 7 in the direction shown by FIG. 6; in this way, diluent passes to the upper chamber 16 and the mixture is produced.

Finally, FIG. 7 shows the double valve closure obtained when the plunger 7, during injection, displaces the mixture towards the outlet nozzle 5.

We claim:

1. A disposable syringe comprising;

an elongated housing means defining a chamber;

a plunger means reciprocally mounted in said housing, said plunger means having a plunger portion, an active head portion and a short portion connecting said plunger portion to said active head portion;

head means sealingly mounted within said chamber for dividing said chamber into a first variable volume chamber and a second variable volume chamber having an outlet means, said head means defining (1) an inner cavity for receiving said active head portion for reciprocal movement of said active head portion within said inner cavity, (2) a first conduit about said short portion for communicating said first variable volume chamber with said inner cavity, and (3) a second conduit for communicating said inner cavity with said second variable volume chamber; and means for reciprocating said plunger means in said housing in (1) a first direction for increasing the volume of the second variable volume chamber wherein a fluid in the first variable volume chamber is communicated from the first variable volume chamber through said first conduit, said inner cavity and said second conduit into said second variable volume chamber, and (2) a second direction for increasing the volume of the first variable volume chamber and decreasing the volume of the second variable volume chamber wherein a fluid in the second variable volume chamber communicates with the outlet means.

2. A syringe according to claim 1 wherein said head means comprises an elastomeric member having a plurality of teeth means projecting into said inner cavity for supporting said active head portion when said plunger means is reciprocated in said first direction.

3. A syringe according to claim 2 wherein said elastomeric member has a semi-spherical cavity which communicates said first variable volume chamber with said first conduit and said plunger has a corresponding semi-spherical portion which seats in said semi-spherical portion of said elastomeric member when said plunger means is reciprocated in said direction for sealing communication between the first variable volume chamber and said second variable volume chamber.

4. A syringe according to claim 3 wherein said active head portion has a projection extending from a body portion for sealing said second conduit wherein said plunger means is reciprocated in said second direction.

5. A syringe according to claim 4 wherein the body portion seals in an inner surface of the elastomeric member defining the inner cavity where said plunger means is reciprocated in said second direction.

* * * * *